(12) United States Patent
Raible et al.

(10) Patent No.: US 10,948,445 B2
(45) Date of Patent: Mar. 16, 2021

(54) METHOD AND GAS SENSOR ARRANGEMENT FOR DETERMINING AN ABSOLUTE GAS CONCENTRATION WITH A GAS SENSOR AND DECOMPOSING GAS TO BE MEASURED

(71) Applicant: Sciosense B.V., AE Eindhoven (NL)

(72) Inventors: Stefan Raible, Tübingen (DE); Simone Scheurer, Reutlingen (DE); Christian Bitterlich, Nehren (DE)

(73) Assignee: SCIOSENSE B.V., AE Eindhoven (NL)

( * ) Notice: Subject to any disclaimer, the term of this patent is extended or adjusted under 35 U.S.C. 154(b) by 185 days.

(21) Appl. No.: 16/303,317

(22) PCT Filed: Apr. 28, 2017

(86) PCT No.: PCT/EP2017/060244
§ 371 (c)(1),
(2) Date: Nov. 20, 2018

(87) PCT Pub. No.: WO2017/202571
PCT Pub. Date: Nov. 30, 2017

(65) Prior Publication Data
US 2019/0212287 A1 Jul. 11, 2019

(30) Foreign Application Priority Data

May 27, 2016 (EP) .................................. 16171757

(51) Int. Cl.
*G01N 27/12* (2006.01)
*G01N 33/00* (2006.01)

(52) U.S. Cl.
CPC ....... *G01N 27/124* (2013.01); *G01N 33/0009* (2013.01); *G01N 33/0016* (2013.01); *G01N 33/0039* (2013.01); *Y02A 50/20* (2018.01)

(58) Field of Classification Search
CPC ............. G01N 27/124; G01N 33/0009; G01N 33/0016; G01N 33/0039; Y02A 50/247
See application file for complete search history.

(56) References Cited

U.S. PATENT DOCUMENTS 3,778,229 A * 12/1973 Webster .................. G01N 27/12
422/98
4,039,941 A * 8/1977 Morrison ................ G01N 27/16
324/71.1

(Continued)

FOREIGN PATENT DOCUMENTS

| DE | 9313992 | 1/1994 | |
|----|---------|--------|--|
| EP | 3163295 A1 * | 5/2017 | ............. G01N 33/02 |
| WO | WO-0014531 A1 * | 3/2000 | ........... G01N 27/124 |

OTHER PUBLICATIONS

Bart, M. et al.: "High Density Ozone Monitoring Using Gas Sensitive Semi-Conductor Sensors in the Lower Fraser Valley, British Columbia" Environmental Science & Technology, vol. 48, No. 7, Apr. 1, 2014, pp. 3970-3977, XP055384309, ISSN:0013-936X, DOI: 10.1021/es404610t.

(Continued)

*Primary Examiner* — Jay Patidar
(74) *Attorney, Agent, or Firm* — Slater Matsil, LLP

(57) ABSTRACT

A method and a gas sensor arrangement for determining an absolute gas concentration with a gas sensor and a decomposing gas to be measured are disclosed. In an embodiment a method includes acquiring a first sensor signal and determining from the first sensor signal at least one initial data point, decomposing the gas to be measured using a means for decomposing the gas of the gas sensor arrangement, acquiring a second sensor signal and determining from the second sensor signal at least one decay data point and deriving an absolute gas concentration from a gas concentration function realized as a mathematical function by (Continued)

evaluating the gas concentration function at least for the at least one initial data point and the at least one decay data point.

20 Claims, 4 Drawing Sheets

(56)     References Cited

U.S. PATENT DOCUMENTS

| | | |
|---|---|---|
| 4,240,799 A | 12/1980 | Ryerson |
| 5,811,662 A | 9/1998 | Williams et al. |
| 6,054,098 A | 4/2000 | Kato et al. |
| 2019/0265183 A1* | 8/2019 | Brown ............... G01N 33/0039 |
| 2019/0271655 A1* | 9/2019 | Graunke .............. G01N 27/123 |

OTHER PUBLICATIONS

European Patent Office, International Search Report for PCT/EP2017/060244, dated Jul. 7, 2017.

Williams, D.E. et al.: "Ozone sensors based on WO 3: A model for sensor drift and a measurement correction method" Meas. Sei. Technol. Meas.Sei. Technol, Jun. 1, 2001 (Jun. 1, 2001), pp. 684-690, XP055384355, Retrieved from the Internet: URL:http://iopscience.iop.org/article/10.1088/0957-0233/12/6/305/pdf.

* cited by examiner

METHOD AND GAS SENSOR ARRANGEMENT FOR DETERMINING AN ABSOLUTE GAS CONCENTRATION WITH A GAS SENSOR AND DECOMPOSING GAS TO BE MEASURED

This invention relates to a method for determining an absolute gas concentration using a gas sensor arrangement and to a gas sensor arrangement for determining an absolute gas concentration.

BACKGROUND OF THE INVENTION

Gas sensors are used to detect the presence of gases in an area, often as part of a safety system. For example, one area of application includes the regular measurement of Ozone content in air and other media. Ozone is a powerful oxidizing agent and can cause a wide range of symptoms in humans, including lacrimation, irritation of the mucous membranes in the mouth, throat, and bronchial tubes, headaches, coughing and even deterioration in lung function. Gas sensors can be used to monitor gas concentration and content in environmental air and can be implemented into systems to alert a user when a gas concentration exceeds hazardous thresholds for humans.

There is an increasing demand to implement gas sensors into mobile applications such as Smartphones, tablets and mobile computers. Thus, gas sensor design seeks to come up with compact and affordable concepts. At the same time, however, the decreasing footprint of gas sensors should not be traded for accuracy. It remains a challenge to combine both compact design and accurate measurement of absolute gas concentration into a single mobile device.

It is to be understood that any feature described below in relation to any one embodiment may be used alone, or in combination with other features described hereinafter, and may also be used in combination with one or more features of any other of the embodiments, or any combination of any other of the embodiments, unless explicitly described as an alternative. Furthermore, equivalents and modifications not described below may also be employed without departing from the scope of the method for determining an absolute gas concentration and the gas sensor arrangement for determining an absolute gas concentration as defined in the accompanying claims.

SUMMARY OF THE INVENTION

In at least one embodiment a method for determining an absolute gas concentration uses a gas sensor arrangement which comprises at least one gas sensor and means for decomposing a gas to be measured. The gas sensor is arranged to generate a sensor signal in response to a gas to be measured. The means for decomposing a gas to be measured is arranged to decompose the gas to be measured into components such as molecules, atoms or ions, for example. The means for decomposing a gas to be measured can be integral or external part of the gas sensor.

Furthermore, the method comprises the following steps. First, a first sensor signal is acquired using the gas sensor. At least one initial data point is determined from the first sensor signal. For example, the data point comprises a resistance value and a time value, which correspond to a resistance measured by the gas sensor at the given time. This examples holds for the case that a resistive gas sensor is used. However, other types of gas sensors can be used as well. Generally, the data points discussed hereinafter comprise a time-resolved measurement value derived from a sensor signal which is provided by the particular gas sensor.

In a next step, the gas to be measured is decomposed using the means for decomposing the gas. For example, the gas is decomposed into chemical components, e.g. components which are not detected by the gas sensor. Then, a second sensor signal is acquired, which is different from the first sensor signal due to the decomposition or decay of the gas, e.g. into one or more components. From the second sensor signal at least one decay data point is determined. For example, the decay data points comprise a resistance value and a timestamp, respectively, which correspond to a resistance measured by the gas sensor at various times, for instance. The decay data points reflect the process of decomposition or decay of the gas into its components.

Finally, an absolute gas concentration is determined from a gas concentration function. This is done by evaluating the gas concentration function at least for the initial data point and one or more decay data points. The term "gas concentration function" relates to a mathematical function by which the data points, determined from the sensor signals, can be evaluated. The evaluation of this function results in a measure for the absolute gas concentration.

For example, the gas concentration function may be a difference function. A difference of decay data points and the initial data point, as a reference, may be proportional to the absolute gas concentration. It may be necessary that additional constraints are met in order to derive an accurate absolute gas concentration from the gas concentration function. For example, the difference gives a more reliable measure of gas concentration if a certain time period lies between acquiring the first and second sensor signals. For example, the second sensor signal could be acquired after the decomposition of the gas reaches a steady state, a characteristic half-value period or a time period at which the decay of gas has reached a certain level.

In general, the term "decomposition of a gas" relates to a process by which the gas is decomposed into components, such as chemical components. For example, Ozone can be chemically decomposed into molecular and atomic oxygen. A decomposition process can be described as a decay and typically is characterized by a certain decay rate. For example, the decomposition of gas may be subject to an exponential decay and the amount of initial gas decreases at a rate proportional to its current value or a characteristic half-value period. In other words, at the time of acquiring the second sensor signal the decomposition may have reached a steady state or may still be in the process of decaying. Furthermore, some decomposition or decay processes can be described as a dynamical equilibrium and the decomposition induced by the means for decomposing seeks to intentionally push the equilibrium to a decay side.

The term "gas sensor arrangement" is used to indicate that the gas sensor and the means for decomposing the gas can be separate or external units. For example, the gas sensor could be implemented as an integrated circuit and the means for decomposing the gas is connected to the integrated circuit. However, there may be embodiments where both components are implemented in one single device such as an integrated circuit comprising both the gas sensor and the means for decomposing the gas.

In at least one embodiment the method for determining an absolute gas concentration is executed in measurement cycles, and the corresponding steps are repeated in each measurement cycle.

In at least one embodiment an absolute Ozone measurement is implemented with an Ozone sensor as gas sensor, in particular with a metal oxide or WO3 gas sensor. The method utilizes Ozone stability during the duration of the measurement.

In at least one embodiment the means for decomposing a gas to be measured comprise a light source. For example, the light source may be an ultra violet light source. The gas is decomposed by means of light to be emitted from the light source. For example, a gas such as Ozone may be formed in an exothermic chemical reaction. The light source may provide sufficient energy to revert forming the gas and decompose the gas into its chemical components.

In at least one embodiment the means for decomposing the gas to be measured comprise a heat source. The gas is decomposed by means of heat to be radiated from the heat source. The heat source could be a component external to the gas sensor, such as an infrared source. Alternatively, or in addition, the gas sensor may have a heater such that can be altered in temperature. The temperature should be set high enough to provide sufficient energy to revert forming of the gas and decompose the gas into its chemical components. For example, a gas such as Ozone may be formed in an exothermic chemical reaction as discussed above and the decomposition is possible if the means for decomposing provide the amount of exothermic energy.

In at least one embodiment the gas concentration function is evaluated by taking a difference between the at least one initial data point and one or more decay data points. In this embodiment the gas concentration function is a difference function and its arguments are data points derived from the gas sensor signals. For example, the initial data point defines a reference point to which the decay data points are compared. The resulting delta, i.e. difference, can result in a value that is proportional or equal to the absolute gas concentration.

In at least one embodiment the gas concentration function is evaluated by interpolating a series of data points. The series of data points is constrained by the initial data point and the at least one decay data point. For example, the initial data point and the at least one decay data point correspond to different sensor signals at different times during the decomposition or decay of the gas to be measured. Data points lying (in time) between (or being constrained by) these points, can be interpolated by means of an interpolation function. Examples include a linear or exponential function. These interpolation functions can be used as gas concentration functions, for example. One possible way to evaluate these functions is to determine their gradients for a given argument. The gradient can result in a value that is proportional or equal to the absolute gas concentration.

In at least one embodiment the decomposition of the gas is monitored using the gas sensor. By monitoring the gas decay a series of decay data points are determined from the sensor signals. The evaluations discussed above may work with at least two data points available, e.g. the initial data point and one decay data point. Monitoring the decomposition or decay of the gas may result in collecting a series of data points which depend on the decay process. For example, the series of decay data points may resemble an exponential decay or a chemical reaction rate equation.

In at least one embodiment the gas concentration function is evaluated by fitting a decay function to a series of data points. The series of data points comprises the series of decay data points and the initial data point. The resulting decay function may resemble an exponential decay or a chemical reaction rate equation, for example. The fitting function can be evaluated, e.g. by determining gradients, slope, etc., in order to determine a value that is proportional or equal to the absolute gas concentration.

In at least one embodiment the gas sensor arrangement comprises one, or a single, gas sensor. The operation of the gas sensor arrangement comprises at least a first, a second and a third phase.

During the first phase the first sensor signal is acquired and from the first sensor signal the at least one initial data point is determined. During execution of the first phase the means for decomposing the gas to be measured are turned off or operated at an initial condition. For example, the initial condition determines a constant temperature or light output which do not yet decompose the gas.

During the second phase the gas to be measured is decomposed, the second sensor signal is acquired and from the second sensor signal the at least one decay data point is determined. During execution of the second phase the means for decomposing the gas to be measured is turned on and operated at a decay condition. For example, at the decay condition the means for decomposing the gas is operated at a constant temperature or light output which is arranged to decompose the gas.

The third phase is executed after the second phase is terminated after a time period. During the third phase the gas is exchanged from the gas sensor arrangement by means of diffusion and/or active air movement. For example, the time period takes into account that decomposition or decay of the gas is not an instant process but rather needs time to reach a certain level or a steady state, for example. The means for decomposing the gas may be operated at the initial condition or any other condition that allows a temperature or light output which does not decompose the gas.

In at least one embodiment the gas sensor arrangement comprises a first gas sensor and a second gas sensor. The at least one initial data point is determined by means of the first gas sensor. The gas to be measured is decomposed at the second gas sensor using the means for decomposing the gas of the gas sensor arrangement. Then, the at least one decay data point is determined by means of the second gas sensor. Finally, the absolute gas concentration is derived from the gas concentration function by evaluating the gas concentration function at least for the initial data point of the first gas sensor and for at least one decay data point of the second gas sensor.

In at least one embodiment the means for decomposing the gas to be measured are provided at the second gas sensor. The first and second gas sensors are operated in different phases. During a first phase the first sensor signal is acquired and from the first sensor signal the at least one initial data point from the first gas sensor is determined. The means for decomposing the gas to be measured are turned off or operated at an initial condition, e.g. a constant temperature or light emission.

During a second phase the gas to be measured is decomposed. The second sensor signal is acquired from the second gas sensor. From the second sensor signal the at least one decay data point is determined with the means for decomposing the gas to be measured turned on or operated at a decay condition e.g. a constant temperature or light emission sufficient to decompose the gas to be measured.

In at least one embodiment the means for decomposing the gas to be measured are provided at both the first and the second gas sensor, and may be activated independently or together. The first, second and third phases of operation are complemented with a fourth, fifth and sixth phase.

In the fourth phase the second gas sensor is used for acquiring the first sensor signal and another initial data point is determined from the first sensor signal. During the fourth phase the means for decomposing the gas to be measured are turned off or operated at an initial condition, e.g. a constant temperature or light emission which do not yet decompose the gas.

During the fifth phase the first gas sensor is used for decomposing the gas to be measured, the second sensor signal is acquired and from the second sensor signal at least another one decay data point is determined. During the fifth phase the means for decomposing the gas to be measured are turned on and operated at a decay condition, e.g. a constant temperature or light emission sufficient to decompose the gas to be measured.

During the sixth phase the fifth phase is terminated after another time period. Then the gas is exchanged from the gas sensor arrangement by means of diffusion and/or active air movement.

In at least one embodiment the gas to be measured is Ozone and the gas sensor comprises an Ozone sensitive gas sensor.

In at least one embodiment a gas sensor arrangement for determining an absolute gas concentration comprises at least one gas sensor which is arranged to generate a sensor signal which is indicative of a gas to be measured. One or more means for decomposing the gas to be measured are provided. The control unit is arranged to operate the gas sensor and the means for decomposing the gas. The control unit is designed to execute the following steps.

The first sensor signal is acquired from the gas sensor and at least one initial data point is determined from the first sensor signal. The gas to be measured is decomposed using the means for decomposing the gas. A second sensor signal is acquired from the gas sensor and at least one decay data point is determined from the second sensor signal.

The gas sensor arrangement further comprises a processing unit which is arranged to determine an absolute gas concentration from a gas concentration function. The gas concentration function is evaluated at least for the initial data point and the decay data point.

In at least one embodiment the means for decomposing the gas to be measured comprises at least one of a heater, a hot plate of the gas sensor, a light source, an ultra violet light source, an infrared source. Furthermore, the gas sensor may comprise at least one of a semiconductor gas sensor, a metal oxide, MOX, gas sensor, a WO3 MOX gas sensor, a resistive gas sensor and/or a chemo-resistive gas sensor.

A semiconductor gas sensor as understood hereinafter is arranged to detect gases by a chemical reaction which takes place when the gas comes in direct contact with the sensor. Tin dioxide or tungsten trioxide are possible materials used in semiconductor gas sensors. For example, the gas sensor such as a semiconductor gas sensor is resistive gas sensor and/or a chemo-resistive gas sensor. Semiconductor gas sensors employ a change in electrical resistance which typically is decreased when the gas sensitive part of the sensor comes in contact with the monitored gas. The resistance of tin dioxide is typically around 50 k$\Omega$ in air but can drop to around 3.5 k$\Omega$ in the presence of 1% methane. The change in resistance can be used to calculate the gas concentration. Semiconductor sensors are commonly used to detect various gases. One use includes detection of Ozone.

In at least one embodiment the gas sensor is located in a sensor package. The sensor package is designed to allow for passive diffusion of the gas to be detected into and/or out of the sensor package. Alternatively, or in addition, the gas sensor arrangement comprises means to provide an active air flow to exchange the gas to be detected away from the gas sensor. The means to provide an active air flow are controlled by means of the control unit.

The aspects presented herein have a number of advantages, including:
- no fan is needed to measure absolute gas concentrations, such as Ozone concentration. Diffusion mechanism can be sufficient to exchange the gas to be measured after a measurement cycle is completed,
- light and/or temperature can be used to decompose the gas, e.g. to destroy Ozone,
- an absolute gas concentration such as Ozone can be determined by measuring a decay time or use a reference point achieved after gas decomposition to derive gas concentration,
- switching between the first and second gas sensor can be used to reduce the need of diffusion and reduce impact of sensor drift.

In at least embodiment Ozone is decomposed, e.g. via light and/or temperature to generate an Ozone free baseline.

In at least embodiment either the decomposition process itself is monitored and used to derive the absolute Ozone concentration (e.g. via measuring the decay time or slope) and/or diffusion, e.g. by means of package design, or active air exchange is used to exchange the decomposed Ozone by fresh surrounding Ozone again and then use the delta between the reference point and the fresh Ozone to derive the absolute Ozone concentration.

In at least embodiment, alternatively or in addition, two sensors are used at different locations to measure Ozone, e.g. one generating the reference point by locally decomposing the Ozone and then measuring the reference concentration, while the other sensor measures the Ozone at the same time at a different location uninfluenced then to generate the absolute value with the measured delta.

Thus, Ozone decomposition can be used as a mechanism for absolute measurement. Hot plates may be used together with additional light and or temperature sources.

An absolute Ozone concentration can be monitored by a time measurement. No active flow is needed. This allows for minimising a device drift by alternative devices used for measurement.

As discussed above a method for decomposition of Ozone can be used to generate referencing baseline to measure absolute. The method may employ a decay time used as absolute measurement reference. Passive diffusion can be used by package design or active air flow to exchange decomposed Ozone by fresh Ozone. A use of two heaters such as hotplates can be used to compensate for drift and/or measure decomposed and fresh Ozone simultaneously at two different locations.

In the following, the concept presented above is described in further detail with respect to drawings, in which exemplary embodiments are presented.

In the exemplary embodiments and Figures below, similar or identical elements may each be provided with the same reference numerals. The elements illustrated in the drawings and their size relationships among one another, however, should not be regarded as true to scale. Rather individual elements, such as layers, components, and regions, may be exaggerated to enable better illustration or improved understanding.

DETAILED DESCRIPTION

Figure 1:
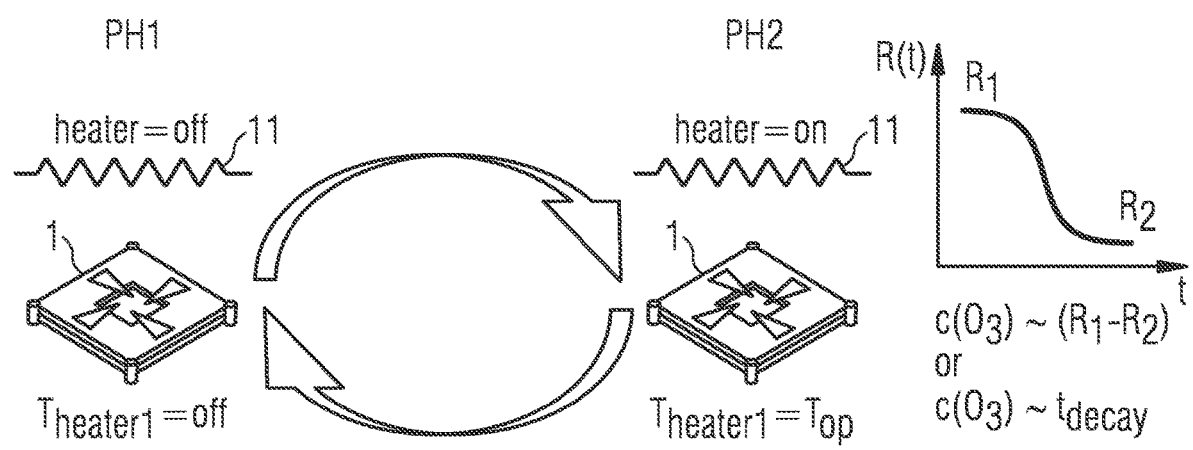
FIG. 1 shows an exemplary embodiment of a gas sensor arrangement having a single gas sensor and a heater.

FIG. 1 shows an exemplary embodiment of a gas sensor arrangement having a single gas sensor 1 and a heater 11. The drawing shows an exemplary use of heat to decay Ozone. For example, Ozone is decomposed by heat originating, e.g. from a sensor hotplate or an external heat source such as an IR source as heaters 11. A decay time $t_{decay}$ characteristic of the Ozone decomposition can be used to derive the absolute Ozone concentration. Furthermore, sensitivity values, such as measured resistance values, obtained by the gas sensor prior Ozone decay and after the decay has been completed can also be used for determining the absolute Ozone concentration. After the Ozone decomposition the Ozone is exchanged by diffusion or active air movement to allow for the next measurement. Package design can support fast air exchange to allow a next cycle to begin.

In particular, the drawing depicts one possible method to determine an absolute Ozone concentration. The method is executed in two consecutive phases. In this particular embodiment, the method employs a resistive MOX gas sensor. The gas sensor 1 comprises a heater 11, e.g. a hotplate or an external heat source, which can be operated at different temperatures.

In a first phase PH1 the heater 11 is operated at an initial condition or at an initial temperature $T_{heater1}$. For example, the heater can be turned off and its temperature settles at ambient temperature $T_{amb}$. Instead the heater 11 can also be operated at a defined operating temperature $T_{op}$, at the operating temperature $T_{op}$ the heater settles has a temperature which is not sufficient to decompose the gas to be measured, e.g. Ozone. The initial condition in the first phase PH1 can be summarized as $T_{heater1}=T_{amb}$ or $T_{op}$.

In a second phase PH2 the heater 11 is turned on or operated at a decay condition, e.g. at a decay temperature $T_{decay}$. At the decay condition the temperature $T_{decay}$ is set high enough to induce a decay or decomposition of Ozone gas, e.g. of gas that is in contact or near vicinity to the gas sensor 1. During the second phase PH2 the resistive MOX gas sensor 1 is used to monitor the Ozone decay. An exemplary measurement curve is depicted on the right side of the drawing. It shows a gas concentration function R(t) as a function of time t. The gas concentration function R(t) is represented by resistance values acquired by the gas sensor 1. The resistance values are data points derived from the sensor signal as a function of time. An initial data point corresponds to a first resistance value R1. Due to the gas decay or decomposition the initial data point decreases in value according to the gas concentration function R(t) and the sensor signal, or decay data points, decrease with time.

The data points collected by means of the resistive MOX gas sensor 1 are indicative of the decay of the Ozone gas and can be evaluated for an absolute ozone concentration. For example, the Ozone gas concentration $c(O_3)$ is proportional to the difference of the first resistance value R1 and a final resistance value R2. The final resistance value R2 is determined after the decay has lasted for a characteristic period of time, such as one decay time $t_{decay}$ or a multiple thereof. The final resistance value R2 can also be determined when the decay of Ozone has reached a steady state.

The first resistance value R1 and the final resistance value R2 can be combined to yield a measure of absolute Ozone gas concentration. For example:

$$c(O_3) \sim (R1-R2).$$

Alternatively, the gas concentration function R(t) can also be evaluated by determining the characteristic decay time $t_{decay}$. This can be achieved by interpolation or fitting a gas concentration function to the data points collected during the decay. The evaluation results in the absolute ozone gas concentration:

$$c(O_3) \sim t_{decay}.$$

Figure 2:
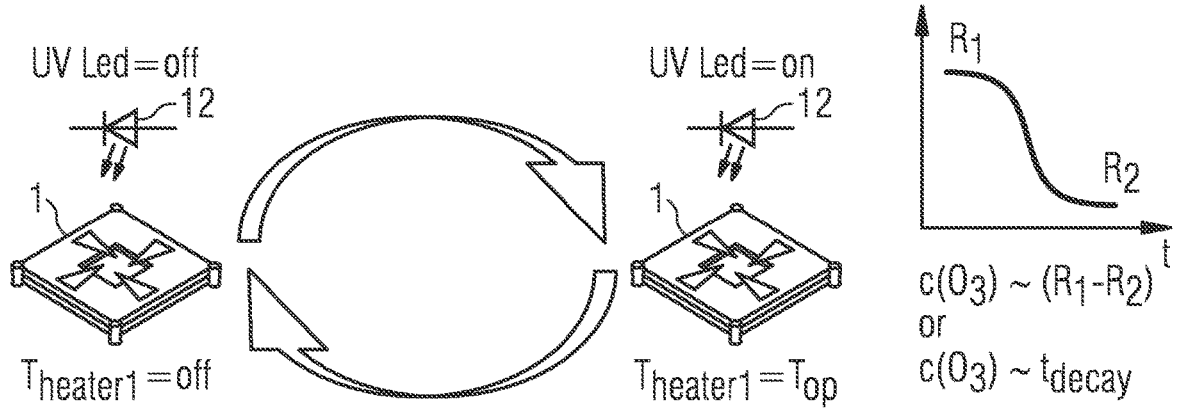
FIG. 2 shows another exemplary embodiment of a gas sensor arrangement having a single gas sensor and a UV light source.

FIG. 2 shows another exemplary embodiment of a gas sensor arrangement having a single gas sensor and a UV light source. The drawings depicts an exemplary use of light to decay Ozone. Operation of the gas sensor arrangement corresponds to the embodiment of FIG. 1. However, in this embodiment a light source 12 is used for decomposing the gas instead of a heater 11. Ozone is decomposed by light originating from the light source, e.g. an external light source such as a UV-B light source or LED. The decay time $t_{decay}$ of Ozone is used to derive the absolute Ozone concentration or the sensitivity values, such as measured resistance values, obtained by the gas sensor 1 prior to Ozone decay and after the decay has been completed. After the Ozone decomposition Ozone is exchanged by diffusion or active air movement to allow for the next measurement. Package design can support fast air exchange to allow a next cycle to begin.

Figure 3:
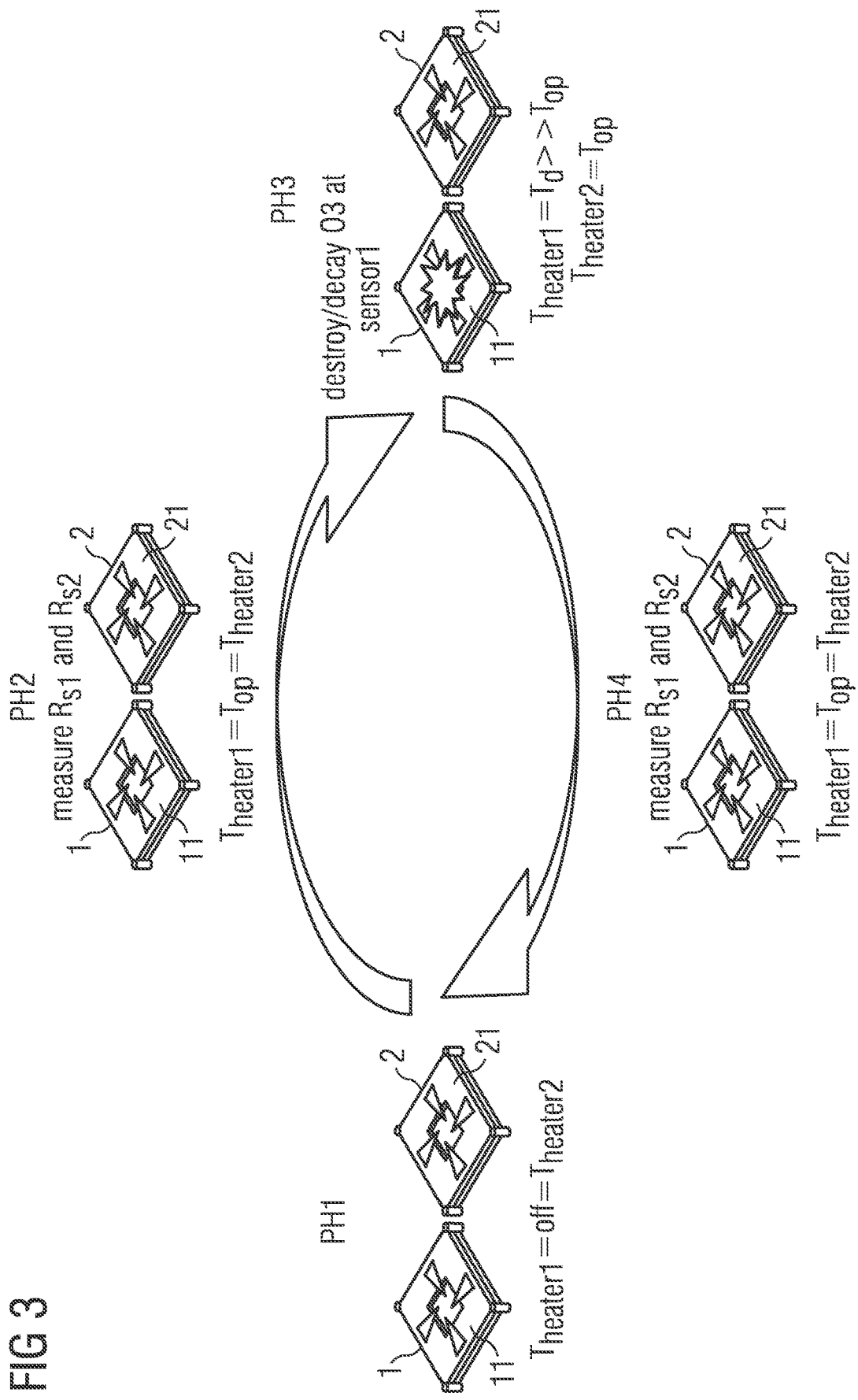
FIG. 3 shows an exemplary embodiment of a gas sensor arrangement having two gas sensors and a hot plate.

FIG. 3 shows an exemplary embodiment of a gas sensor arrangement having two gas sensors and a hot plate as heater. The drawings depicts an exemplary use of two gas sensors 1, 2 to measure Ozone. Ozone is decomposed by heat originating from a first sensor hotplate 11, which is integrated into the gas sensor. A second hotplate 21, which is integrated into the second gas sensor 2 is placed at a different location and is used to measure an undistracted Ozone concentration.

To derive the absolute Ozone concentration the sensor signals and corresponding data values of both gas sensors 1, 2 are used as opposed to using sensor signals and corresponding data values from a single gas sensor as discussed with respect to FIGS. 1 and 2. For example, the absolute Ozone gas concentration can be proportional to the delta, e.g. a difference, of resistance readings, for the two gas sensors 1, 2. After the Ozone decomposition the Ozone is exchanged by diffusion or active air movement to allow the next measurement. Package design can support fast air exchange to allow a next cycle to begin.

The gas sensor arrangement of FIG. 3 is operated in different phases. In a first phase PH1 both gas sensors 1, 2 are set to an initial condition. For example, both gas sensors 1, 2, i.e. both heaters 11, 21, such as sensor hot plates, are turned off or operated at an initial operating temperature. The initial temperature could be equal to the ambient temperature $T_{amb}$ or, alternatively, be equal to an operation temperature $T_{op}$. The latter could be established by regulating the heaters to a temperature which is not yet sufficient to decompose the gas to be measured. This can be summarized as $T_{heater1}=(T_{amb}, T_{op})=T_{heater2}$. Both gas sensors remain in phase PH1 long enough that Ozone diffuses to the two gas sensors at two different locations.

In a second phase PH2 both gas sensors measure a gas background at an operation temperature. Both heaters 11, 21, e.g. sensor hot plates, are set to the operation temperature $T_{op}$, i.e. $T_{heater1}=T_{op}=T_{heater2}$. The operation temperature $T_{op}$ is not sufficient to decompose the gas to be measured. In this condition sensor signals are acquired by the gas sensors 1, 2, respectively. In this particular embodiment the resistive MOX gas sensors acquire from the sensor signals first resistance values $R_{s1}$ and $R_{s2}$, respectively. Alternatively, the first and second phases PH1, PH2 could be combined into a single phase and the heaters 11, 21 set to an initial temperature $T_{heater1}=T_{heater2}=T_{amb}$ or $T_{op}$, which could be equal to the ambient temperature $T_{amb}$ or, alternatively, be equal to the operation temperature $T_{op}$.

In a third phase PH3 the heater 11 of the first gas sensor 1 is set to a temperature high enough to induce decay or decomposition of the Ozone gas. Typically the decay temperature $T_{decay}$ is set to a much higher value than the operating temperature $T_{op}$: $T_{decay} \gg T_{op}$. At the same time the temperature of the second gas sensor 2 is held at the operating temperature $T_{op}$. The gas sensor arrangement stays in phase PH3 for a certain time. The time may be determined by the decay process. For example, the gas sensor arrangement may proceed with a next phase after the decay has lasted for a characteristic period of time, such as one decay time $t_{decay}$ or a multiple thereof. The next phase can also be entered when the decay of Ozone has reached a steady state.

In a fourth phase PH4 the gas sensor arrangement returns to the conditions defined for phase PH2. This effectively terminates the decomposition of Ozone. The resistive gas sensors 1, 2 measure the gas background at the operation temperature $T_{op}$ and then acquire final resistance values $R_{f1}$ and $R_{f2}$, respectively. The absolute Ozone concentration can be determined from the first resistance values $R_{s1}$ and $R_{s2}$ and final resistance values $R_{f1}$ and $R_{f2}$. For example, a resistance difference can be constructed and made proportional to the absolute Ozone concentration $c(O_3)$. This yields:

$$c(O_3) \sim (R_{s1}-R_{f1}) - (R_{s2}-R_{f2}).$$

After the fourth phase PH4 the gas sensor arrangement may return to the first phase and start another measurement cycle. After the Ozone decomposition the Ozone is exchanged by diffusion or active air movement the next measurement cycle can start. Typically, the gas sensor arrangement stays in phase PH1 for an off-time, Off, which is chosen long enough to allow Ozone diffusion to settle at environmental level again. Package design can support fast air exchange to allow a next cycle to begin.

Alternatively, the two gas sensors can be switched (see FIG. 4) or light sources can be used instead, or in addition, to the heaters. Furthermore, instead of measuring resistance values before and after the decomposition, also the decay process can be monitored and fitted by an appropriate gas concentration function. Exemplary parameters are $T_{op}$=optimum WO3 gas sensor temperature for operation, $T_d$=temperature to decay O3 concentration.

Figure 4:
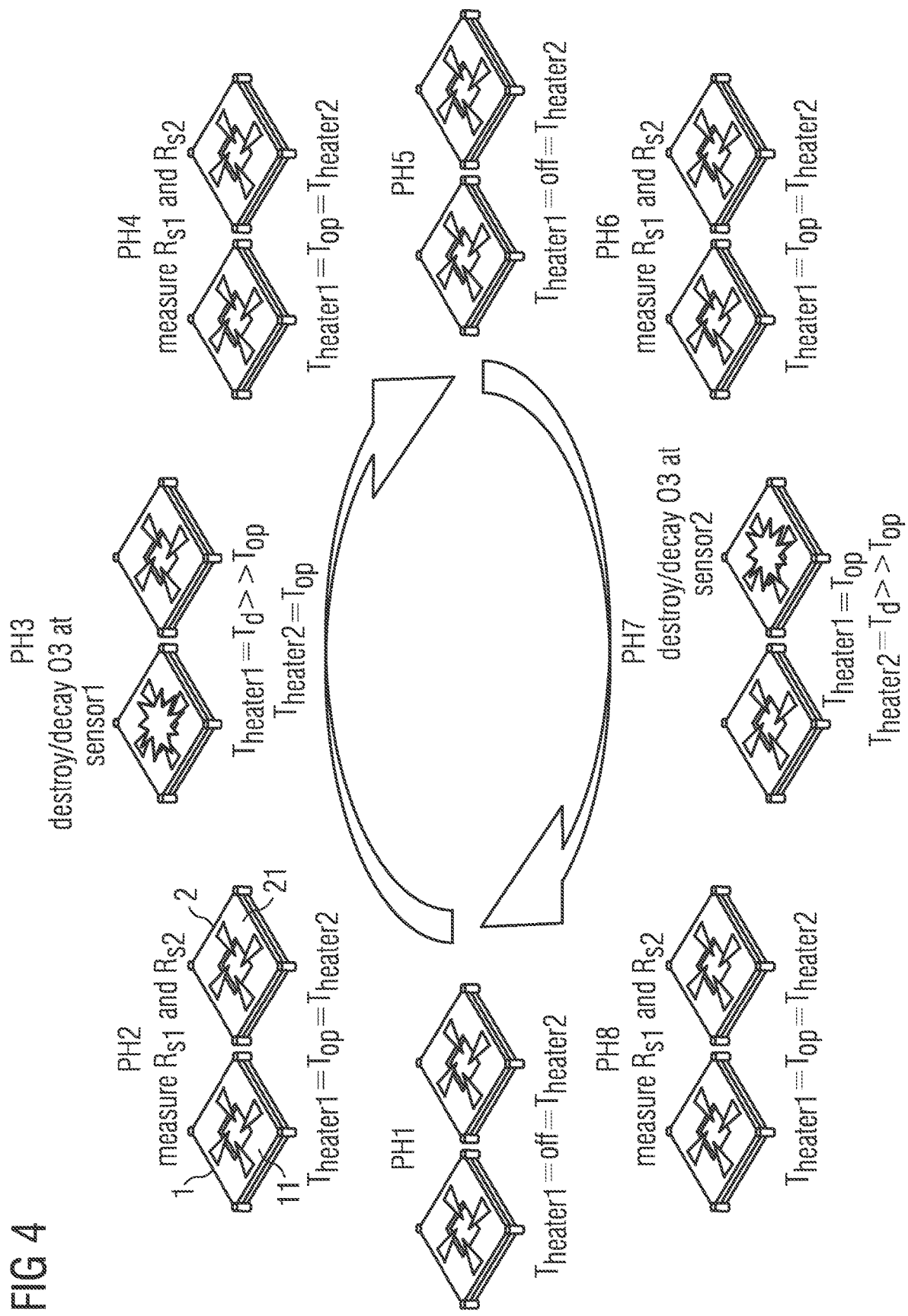
FIG. 4 shows an exemplary embodiment of a gas sensor arrangement having two gas sensors and two hot plates.

FIG. 4 shows an exemplary embodiment of a gas sensor arrangement having two gas sensors 1, 2 and two hot plates 11, 21 (reference numerals are only shown for the phase PH2 for better representation). The drawing depicts an exemplary use of two sensors to measure Ozone and alternate sensor for decay to minimize drift. This embodiment corresponds to the one shown in FIG. 3 only the gas sensors are alternatingly used to decompose the Ozone at different locations. This can be used to compensate for drift issues as both sensors see the same thermal history over time. This approach involves symmetric drift switch between gas sensors.

Briefly, the method in this embodiment involves eight phases. Phases PH1 to PH4 correspond to phases PH1 to PH4 of FIG. 3. After phase PH4, however, the gas sensor arrangement does not return to phase PH1 directly. Instead a fifth, sixth, seventh and eights phase PH5, PH6, PH7, PH8 are consecutively executed. These phases PH5 to PH8 correspond to phases PH1 to PH4 but with the gas sensors exchanged, i.e. during the first four phases PH1 to PH4 the first gas sensor 1 is used for decomposing, and then the second four phases PH5 to PH8 the second gas sensor 2 is used for decomposing the gas.

Figure 5:
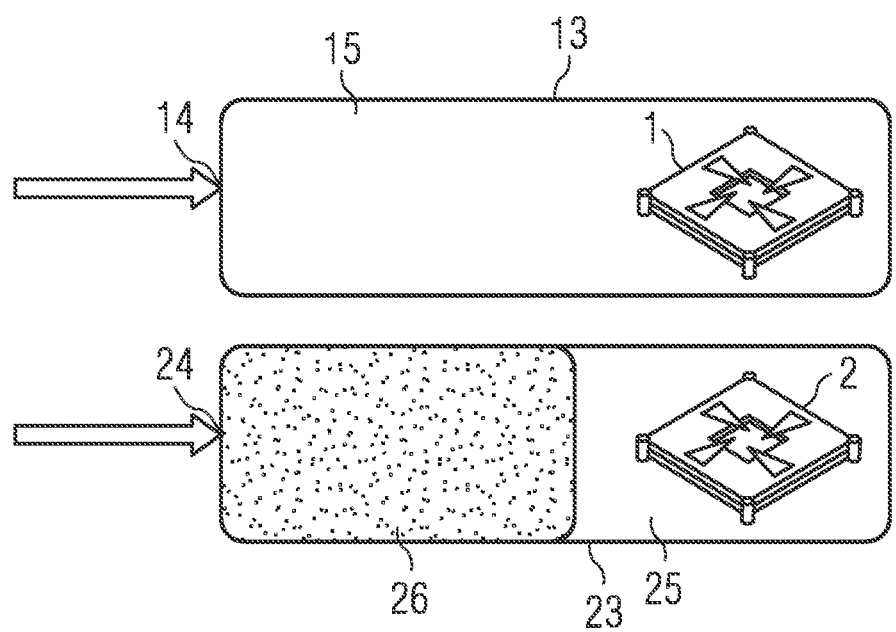
FIG. 5 shows an exemplary embodiment of a gas sensor arrangement having a charcoal trap.

FIG. 5 shows an exemplary embodiment of a gas sensor arrangement having a charcoal trap. The drawing depicts an exemplary Ozone sensor comprising a first gas sensor 1 and a second gas sensor 1 which is arranged to destroy Ozone gas locally by heat.

In this particular embodiment the first gas sensor 1 is a MOX gas sensor which is based on a resistive operation principle. The gas sensor 1 is arranged inside the sensor package 13 having a first gas inlet 14. Ozone gas can diffuse into and out of the package 13 via the first gas inlet 14. The sensor package 13 has no dedicated ozone gas filter. The second gas sensor 2 is also a MOX gas sensor and detects the presence of gas by changing its resistance. The second gas sensor is also arranged inside a sensor package 23 and has a second gas inlet 24. Both the first and second gas sensors 1, 2 can be arranged in the same sensor package but separated from each other. However, the sensor packages 13, 23 can also be two separated units. The gas sensors are embedded in respective cavities 15, 25 which are independent from each other.

Furthermore, a charcoal trap 26 is arranged inside the sensor package 23 of the second gas sensor 2. Ozone gas entering or leaving the cavity 25 of the second gas sensor 2 needs to travel through the charcoal trap 26. The charcoal trap 26 can be activated (activated charcoal) and set to a certain operating temperature. This way the charcoal trap 26 can serve as a heater 21 as discussed in the embodiments above. The gas sensor arrangement of FIG. 5 can thus be used as gas sensor arrangement in one or more of the embodiments of FIGS. 1 to 4 discussed above.

Resistive MOX gas sensors can be assumed to have a constant sensitivity over the time periods involved in measuring the absolute ozone gas concentration. This fact supports that a differential measurement conducted with the first and second gas sensors and respective resistance values can be used as a measure which is proportional to the absolute ozone gas concentration.

Ozone measurement cycle could involve the following steps:

1. Both sensors off=off long enough that 03 diffuses to sensors (sensor 1 and 2 at two different locations).
2. Sensor 1 and 2 measure gas background at operation temperature.
3. Sensor 1 operates at high temp to destroy Ozone.
4. Sensor 1 and 2 measure gas background at operation temperature. Difference of resistance is proportional to the Ozone concentration.
5. Back to point 1

Two hotplates can be used. However, humidity and other environmental items are changed and power consumption needs to be provided. UV as a light source can be very specific and will only destroy O3, for example. Power consumption can be lower, e.g. using a LED. However, an UV source is needed.

The proposed concept above can be miniaturised and used within low power measurement applications for consumer (IoT, wearables, mobile), industrial and automotive applications. With tailored package design a miniaturised device is seen possible.

The following items further support the proposed approach, for example:
- use O3 decay together with sensor, e.g. a WO3 sensor, to measure an absolute O3 concentration,
- WO3 Mox sensitivity may be stable over time,
- O3 typically decays faster and at known rate in air at higher temperatures or/and under UV B exposure in air,
- resistance delta can be used to measure Ozone concentration based on known decay rate.

The embodiments discussed above relate to measurement of an absolute Ozone as the gas to be measured. Ozone can be created by photochemical reactions involving molecular oxygen O2. For example, when diatomic oxygen absorbs ultraviolet radiation with wavelengths less than 240 nm, it breaks apart into two oxygen atoms:

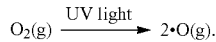

The resulting oxygen atoms combine with O2 molecules to form Ozone:

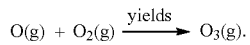

This reaction is exothermic. In turn, Ozone absorbs ultraviolet radiation with wavelengths as long as 290 nm. This radiation causes the Ozone to decompose into $O_2$ molecules and oxygen atoms:

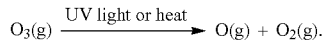

This, too, is an exothermic reaction. Thus, radiation and heat can be used to decompose Ozone into its components. This effect is employed in the method discussed so far.

Nevertheless, the methodology is not restricted to Ozone but can be applied to all gases which can be decomposed by means of heat and/or radiation.

The invention claimed is:

1. A method for determining an absolute gas concentration, using a gas sensor arrangement comprising a gas sensor and means for decomposing a gas to be measured, the method comprising:
   acquiring a first sensor signal and determining from the first sensor signal at least one initial data point;
   decomposing the gas to be measured using the means for decomposing the gas of the gas sensor arrangement;
   acquiring a second sensor signal and determining from the second sensor signal at least one decay data point; and
   deriving the absolute gas concentration from a gas concentration function realized as a mathematical function by evaluating the gas concentration function at least for the at least one initial data point and the at least one decay data point,
   wherein a decomposition of the gas is monitored using the gas sensor and by determining a series of decay data points from the second sensor signal,
   wherein the gas concentration function is evaluated by fitting a decay function to a series of data points comprising the series of decay data points and the at least one initial data point, and
   wherein the decay function resembles an exponential decay or a chemical reaction rate equation.

2. The method according to claim 1, wherein the means for decomposing the gas to be measured comprise a light source or an ultra violet light source, and wherein the gas is decomposed by light to be emitted from the light source.

3. The method according to claim 1, wherein the means for decomposing the gas to be measured comprise a heat source, and wherein the gas is decomposed by heat to be radiated from the heat source.

4. The method according to claim 1, wherein the gas concentration function is evaluated by taking a difference between the at least one initial data point and one or more decay data points.

5. The method according to claim 1, wherein the gas concentration function is evaluated by interpolating a series of data points constrained by the at least one initial data point and the at least one decay data point.

6. The method according to claim 1,
   wherein the gas sensor arrangement comprises one gas sensor,
   wherein acquiring the first sensor signal and determining from the first sensor signal the at least one initial data point is executed during a first phase with the means for decomposing the gas to be measured turned off or operated at an initial condition,
   wherein decomposing a gas to be measured, acquiring the second sensor signal and determining from the second sensor signal the at least one decay data point is executed during a second phase with the means for decomposing the gas to be measured turned on and operated at a decay condition, and
   wherein the second phase is terminated after a time period and the gas is exchanged from the gas sensor arrangement by diffusion and/or active air movement in a third phase.

7. The method according to claim 1, wherein the gas to be measured is Ozone and the gas sensor comprises an Ozone gas sensor.

8. A method for determining an absolute gas concentration, using a gas sensor arrangement comprising a gas sensor, a further gas sensor and means for decomposing a gas to be measured, the method comprising:
   acquiring a first sensor signal and determining from the first sensor signal at least one initial data point;
   decomposing the gas to be measured using the means for decomposing the gas of the gas sensor arrangement;
   acquiring a second sensor signal and determining from the second sensor signal at least one decay data point; and
   deriving the absolute gas concentration from a gas concentration function realized as a mathematical function by evaluating the gas concentration function at least for the at least one initial data point and the at least one decay data point,
   wherein the at least one initial data point is determined by the gas sensor,
   wherein the gas to be measured is decomposed at the further gas sensor using the means for decomposing the gas of the gas sensor arrangement, wherein the at least one decay data point is determined by the further gas sensor, and
wherein the absolute gas concentration is derived from the gas concentration function by evaluating the gas concentration function at least for the at least one initial data point of the gas sensor and for at least one decay data point of the further gas sensor.

9. The method according to claim 8,
wherein the means for decomposing the gas to be measured is provided at the further gas sensor,
wherein acquiring the first sensor signal and determining from the first sensor signal the at least one initial data point from the gas sensor is executed during a first phase with the means for decomposing the gas to be measured turned off or operated at an initial condition,
wherein decomposing the gas to be measured, acquiring the second sensor signal from the further gas sensor and determining from the second sensor signal the at least one decay data point is executed during a second phase with the means for decomposing the gas to be measured turned on and operated at a decay condition, and
wherein the second phase is terminated after a time period and the gas is exchanged from the gas sensor arrangement by diffusion and/or active air movement in a third phase.

10. The method according to claim 9,
wherein the means for decomposing the gas to be measured is provided at both the gas sensor and the further gas sensor,
wherein the first, second and third phases are complemented with a fourth, fifth and sixth phases,
wherein, in the fourth phase the further gas sensor is used for acquiring the first sensor signal and determining another initial data point from the first sensor signal with the means for decomposing the gas to be measured turned off or operated at an initial condition,
wherein, in the fifth phase the gas sensor is used for decomposing the gas to be measured, acquiring the second sensor signal and determining from the second sensor signal at least another one decay data point with the means for decomposing the gas to be measured turned on and operated at a decay condition, and
wherein, in the sixth phase the fifth phase is terminated after another time period and the gas is exchanged from the gas sensor arrangement by diffusion and/or active air movement.

11. A gas sensor arrangement for determining an absolute gas concentration comprising:
at least one gas sensor configured to generate a sensor signal indicative of a gas to be measured;
one or more means for decomposing the gas to be measured;
a control unit configured to operate the gas sensor and the means for decomposing the gas such that:
a first sensor signal is acquired from the gas sensor and at least one initial data point is determined from the first sensor signal, the gas to be measured being decomposed using the means for decomposing the gas, and
a second sensor signal is acquired from the gas sensor and at least one decay data point is determined from the second sensor signal; and
a processing unit configured to determine an absolute gas concentration from a gas concentration function realized as a mathematical function by evaluating the gas concentration function at least for the at least one initial data point and the at least one decay data point, wherein a decomposition of the gas is monitored using the gas sensor and by determining a series of decay data points from the second sensor signal,
wherein the gas concentration function is evaluated by fitting a decay function to a series of data points comprising the series of decay data points and the at least one initial data point, and
wherein the decay function resembles an exponential decay or a chemical reaction rate equation.

12. The gas sensor arrangement according to claim 11,
wherein the means for decomposing the gas to be measured comprises at least one of:
a heat source, a heater, a hot plate of the gas sensor, a light source, an ultra violet light source, or an infrared source, and/or
wherein the gas sensor comprises at least one of:
a semiconductor gas sensor, a metal oxide, MOX, gas sensor, a $WO_3$ MOX gas sensor, a resistive gas sensor or a chemo-resistive gas sensor.

13. The gas sensor arrangement according to claim 11,
wherein the gas sensor is located in a sensor package designed to allow for passive diffusion of the gas to be detected into and/or out of the sensor package, and/or
wherein the gas sensor arrangement comprises means for providing an active air flow to exchange the gas to be detected away from the gas sensor and under control of the control unit, and/or
wherein the gas sensor arrangement comprises a charcoal trap as heat source.

14. A gas-sensor arrangement for determining an absolute gas concentration comprising:
at least one gas sensor configured to generate a sensor signal indicative of a gas to be measured;
one or more means for decomposing the gas to be measured;
a control unit configured to operate the at least one gas sensor and the means for decomposing the gas such that:
a first sensor signal is acquired from the at least one gas sensor and at least one initial data point is determined from the first sensor signal, the gas to be measured being decomposed using the means for decomposing the gas, and
a second sensor signal is acquired from the at least one gas sensor and at least one decay data point is determined from the second sensor signal; and
a processing unit configured to determine an absolute gas concentration from a gas concentration function realized as a mathematical function by evaluating the gas concentration function at least for the at least one initial data point and the at least one decay data point,
wherein the at least one gas sensor comprises a gas sensor and a further gas sensor,
wherein the at least one initial data point is determined by the gas sensor,
wherein the gas to be measured is decomposed at the further gas sensor using the means for decomposing the gas of the gas sensor arrangement,
wherein the at least one decay data point is determined by the further gas sensor, and
wherein the absolute gas concentration is derived from the gas concentration function by evaluating the gas concentration function at least for the at least one initial data point of the gas sensor and for at least one decay data point of the further gas sensor.

15. The gas sensor arrangement according to claim 14,
wherein the means for decomposing the gas to be measured comprises at least one of a heat source, a heater, a hot plate of the gas sensor, a light source, an ultra violet light source, or an infrared source.

16. The gas sensor arrangement according to claim 14, wherein the gas sensor comprises at least one of a semiconductor gas sensor, a metal oxide, MOX, gas sensor, a $WO_3$ MOX gas sensor, a resistive gas sensor or a chemo-resistive gas sensor.

17. The gas sensor arrangement according to claim 16, wherein the means for decomposing the gas to be measured comprises at least one of a heat source, a heater, a hot plate of the gas sensor, a light source, an ultra violet light source, or an infrared source.

18. The gas sensor arrangement according to claim 14, wherein the gas sensor is located in a sensor package designed to allow for passive diffusion of the gas to be detected into and/or out of the sensor package.

19. The gas sensor arrangement according to claim 14, further comprising means for providing an active air flow to exchange the gas to be detected away from the gas sensor and under control of the control unit.

20. The gas sensor arrangement according to claim 14, wherein the means for decomposing the gas comprises a charcoal trap as heat source.

* * * * *